United States Patent
Oonuma et al.

(10) Patent No.: US 7,050,165 B2
(45) Date of Patent: May 23, 2006

(54) ATOMIC ABSORPTION SPECTROPHOTOMETER

(75) Inventors: Mitsuru Oonuma, Tokyo (JP); Yoshimi Kasai, Funabashi (JP); Hayato Tobe, Mito (JP)

(73) Assignee: Hitachi Naka Instruments Co., Ltd., Ibaraki (JP)

( * ) Notice: Subject to any disclaimer, the term of this patent is extended or adjusted under 35 U.S.C. 154(b) by 104 days.

(21) Appl. No.: 10/767,443

(22) Filed: Jan. 30, 2004

(65) Prior Publication Data

US 2004/0184034 A1    Sep. 23, 2004

(30) Foreign Application Priority Data

Jan. 30, 2003    (JP)    ............................. 2003-022390

(51) Int. Cl.
*G01N 21/31*    (2006.01)
(52) U.S. Cl. ..................... 356/319; 356/312; 356/315
(58) Field of Classification Search ................ 356/312, 356/315, 319
See application file for complete search history.

(56) References Cited

FOREIGN PATENT DOCUMENTS

| JP | 5-306996 | * | 11/1993 |
|----|----------|---|---------|
| JP | 6-58870 | * | 3/1994 |
| JP | 10-73536 | | 8/1996 |

* cited by examiner

*Primary Examiner*—F. L. Evans
(74) *Attorney, Agent, or Firm*—Reed Smith LLP; Stanley P. Fisher, Esq.; Juan Carlos A. Marquez, Esq.

(57) ABSTRACT

A main unit, a lamp chamber, a graphite furnace analyzing section, a flame analyzing section, and a flame gas controller are sequentially placed from right to left. An autosampler is placed on the top of the lamp chamber. A housing section for a transformer and a power supply unit is provided behind the lamp chamber, the graphite furnace analyzing section, the flame analyzing section, and the flame gas controller. The housing section is used as a space for a power unit used for the whole atomic absorption spectrophotometer, as well as the graphite furnace analyzing section. The housing section is also used as space for a circuit board for controlling the whole atomic absorption photometer. The autosampler has a quadrangular sample tray. The autosampler drives an arm for holding an aspiration needle in the left and right directions and also in up and down directions.

9 Claims, 13 Drawing Sheets

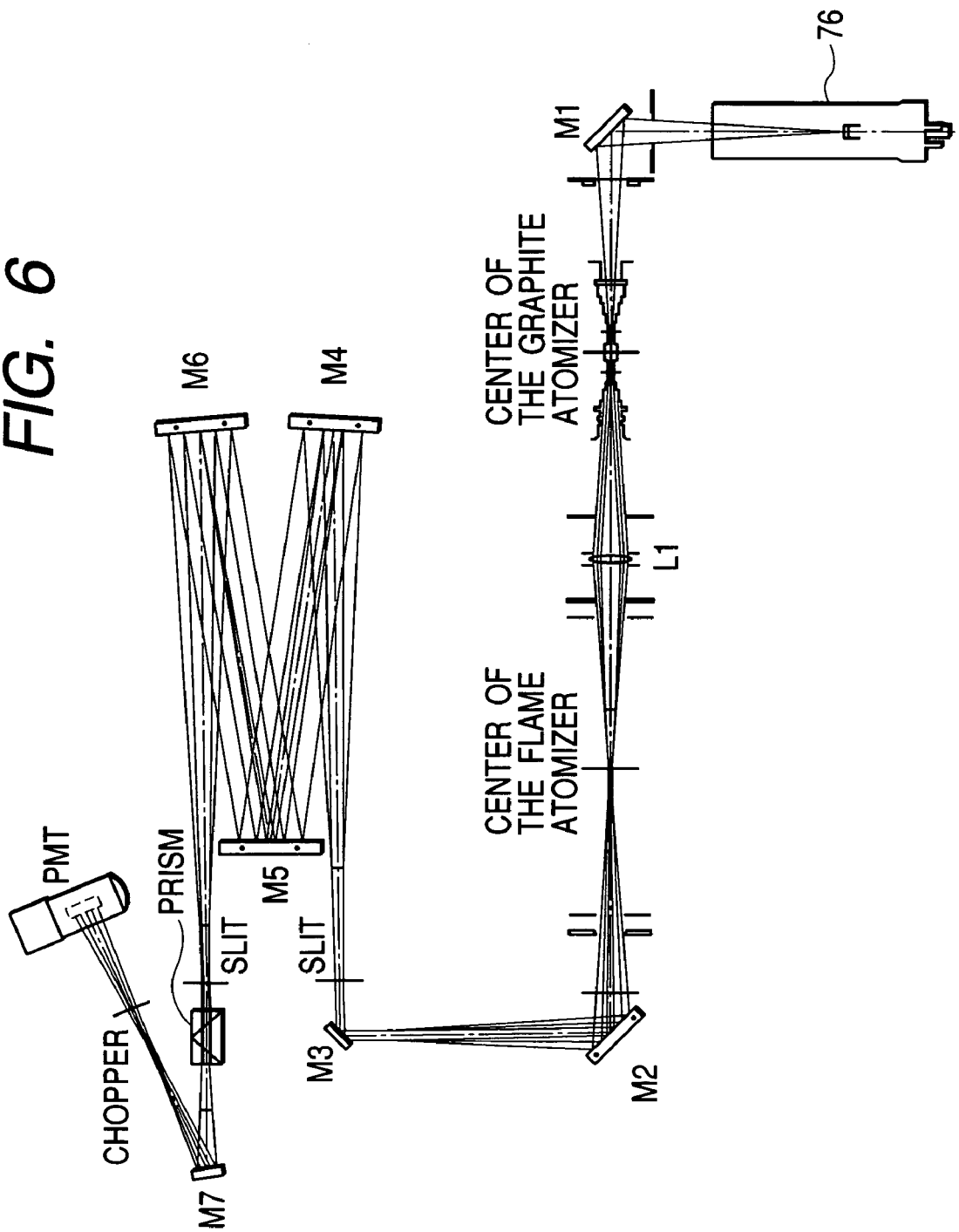

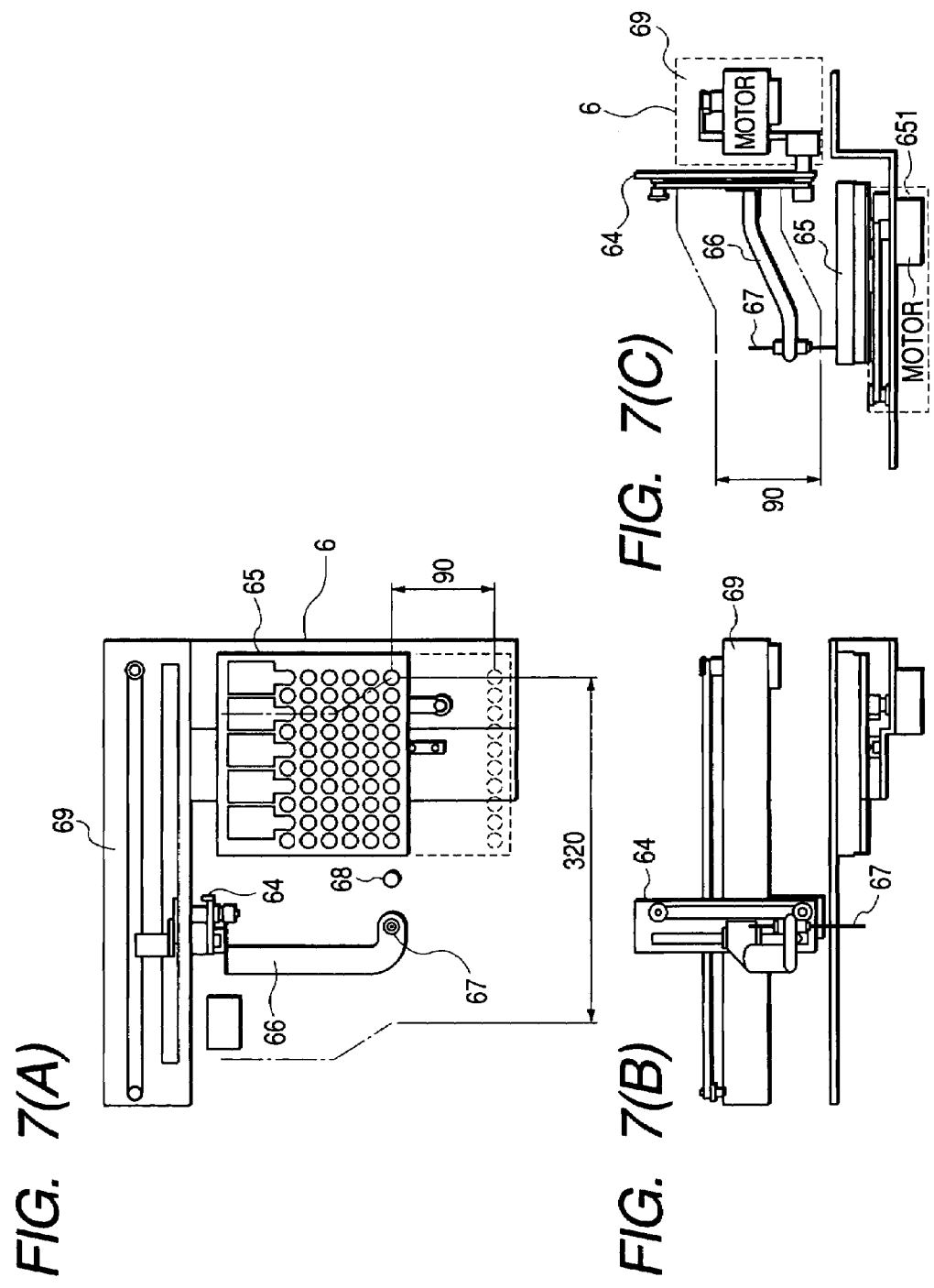

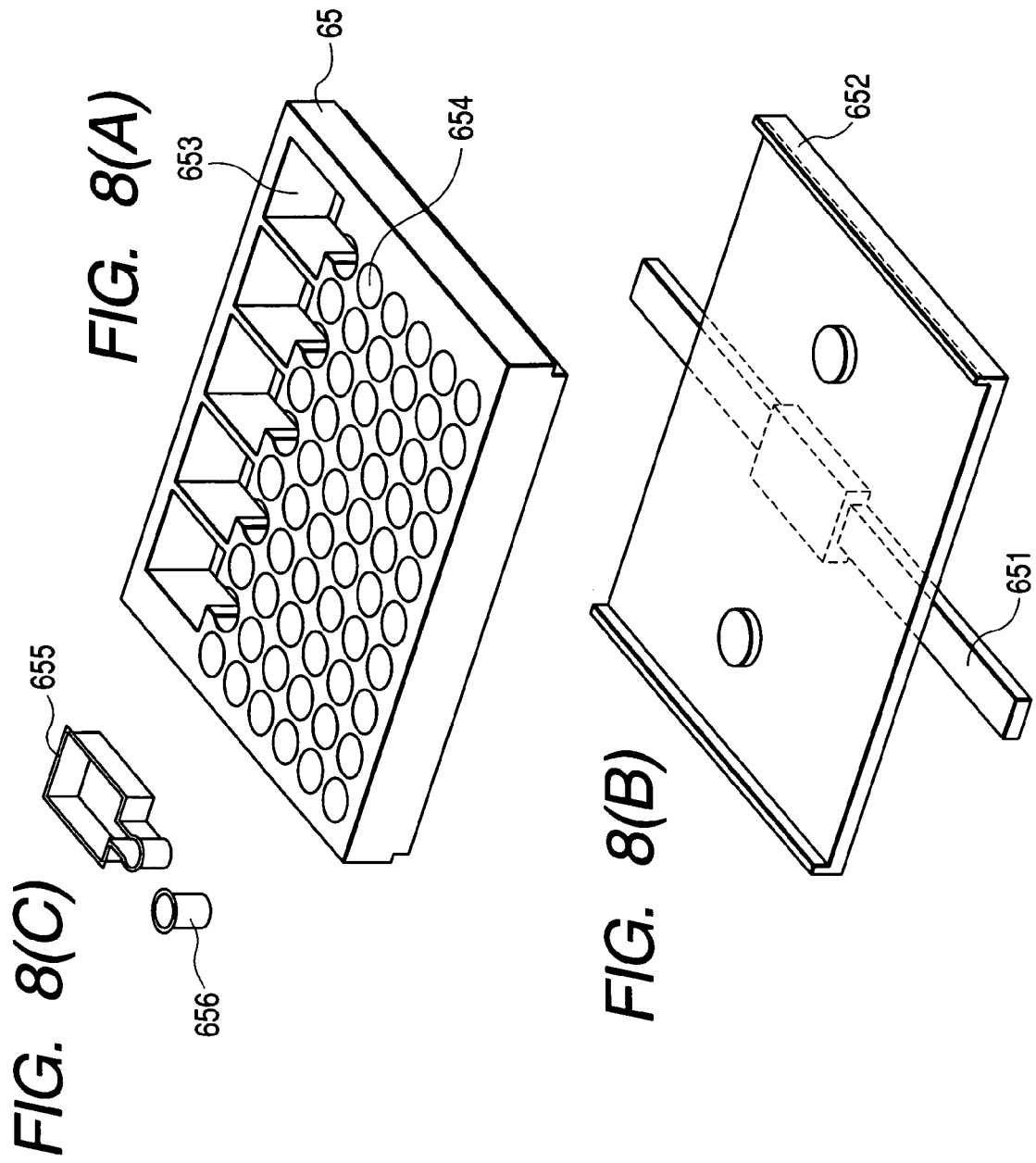

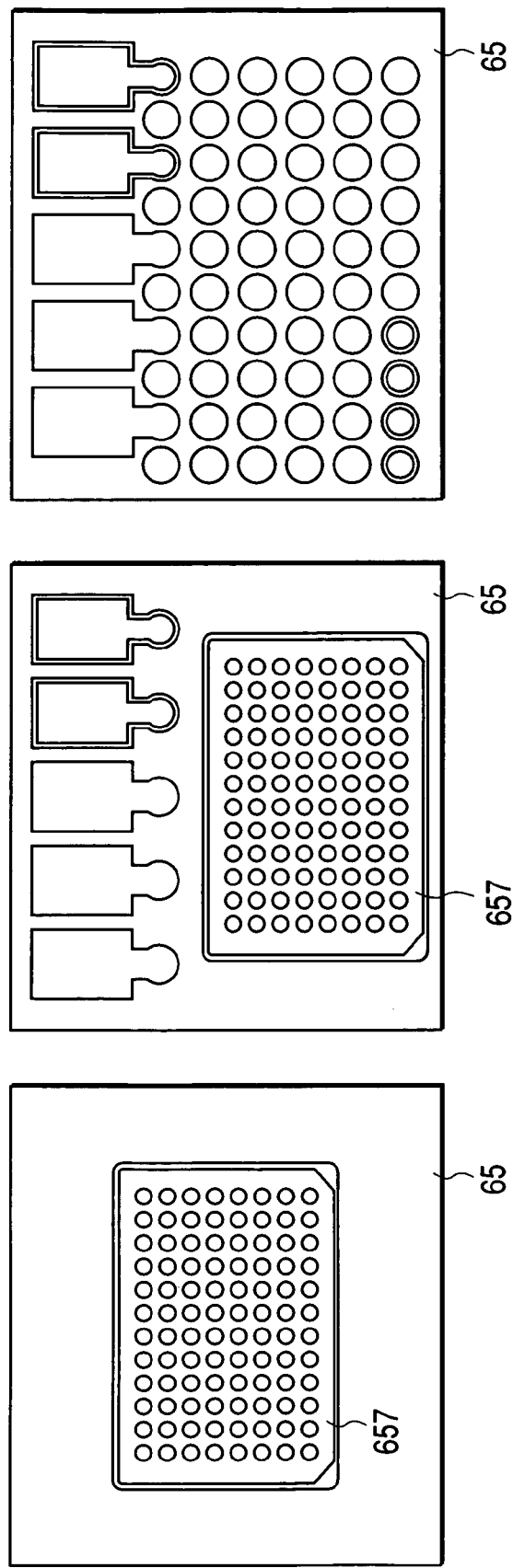

ATOMIC ABSORPTION SPECTROPHOTOMETER

BACKGROUND OF THE INVENTION

The present invention relates to an atomic absorption spectrophotometer, and more particularly to a small-sized atomic absorption spectrophotometer comprising either a graphite furnace analyzing section or a flame analyzing section, or comprising both of them.

Atomic absorption spectrophotometers are generally used for the quantitative analysis of metal including heavy metals, it is well-known that the spectrophotometers is used for the following analysis methods. In the flame analyzing method, a sample including metal to be analyzed is sprayed into combustion flame such as acetylene flame to atomize the sample. A luminous flux having a wavelength which is absorbed by the metal to be analyzed is passed through the flame. Detecting attenuation of the luminous flux, the quantity of the metal included in the sample is detected. In the graphite furnace analyzing method, a sample is dropped into a heated graphite pipe to vaporize and atomize the sample. And then, same as above-mentioned method, a luminous flux having a wavelength which is absorbed by the metal to be analyzed is passed through the graphite pipe. Detecting attenuation of the luminous flux, the quantity of the metal included in the sample is detected.

Concerning the kinds of metals which can be analyzed, there is a different territory between the flame analyzing method and the graphite furnace analyzing method. And lengths of time required for the analyses also differ between both of the methods. Therefore, generally, the atomic absorption spectrophotometers are so devised that analyses by both of the methods are possible.

FIG. 13 is a perspective view illustrating a configuration of an atomic absorption spectrophotometer according to the prior art. FIG. 14 is a diagram illustrating a state inside a lamp chamber. In FIGS. 13 and 14, reference numeral 1 denotes a main unit; reference numeral 2 denotes a lamp chamber; reference numeral 3 denotes a graphite furnace analyzing section; reference numeral 4 denotes a flame analyzing section; reference numeral 5 denotes an electric control section; reference numeral 6 denotes an autosampler; reference numeral 7 denotes a graphite furnace power supply section; reference numeral 8 denotes a cooling drain pot; reference numeral 21 denotes a door; reference numeral 22 denotes a switch; reference numeral 23 denotes an indicator; reference numeral 76 denotes lamps; and reference numeral 77 denotes a lamp holder.

As shown in FIG. 13, inside the main unit 1 of the atomic absorption spectrophotometer according to the prior art, the lamp chamber 2 equipped with the door 21 having a clear window is placed on the right side. The graphite furnace analyzing section 3 to which the autosampler 6 is connected, the flame analyzing section 4, and the electric control section 5 are sequentially placed in the left direction from a position next to the lamp chamber 2. The graphite furnace power supply section 7 is placed behind them. The autosampler 6 is a device by which using a micropipette. A sample to be analyzed is automatically dropped into a cylindrical heater made of graphite, which is called a cuvette of the graphite furnace analyzing section 3. Using the autosampler 6, it becomes possible to automatically and successively analyze a large number of samples.

In the example shown in FIG. 13, in the lower part of the flame analyzing section 4, a device for blowing a sample into the flame analyzing section 4 is provided at a position of the door opening downward. The flame analyzing section 4 can also be provided with an autosampler having the same functions as above although such an autosampler is not illustrated in the figure. Moreover, the whole atomic absorption spectrophotometer according to the prior art is controlled and operated by a personal computer, which is installed next to the main unit 1.

The door 21, the switch 22, the indicator 23 etc. are placed on the front of the lamp chamber 2. The door 21 is equipped with a clear window. Operating states of the hollow cathode lamps 76 placed inside, and the like, can be checked through the window.

As shown in FIG. 14, the plural hollow cathode lamps 76, which are attached to the turret-type lamp holder 77, are placed in the lamp chamber 2. Each of the hollow cathode lamps 76 corresponds to a metallic atom to be detected. The hollow cathode lamps 76 are attached to the lamp holder 77 perpendicularly, that is to say, in the vertical direction so that the hollow cathode lamps 76 are replaceable and their emission surfaces of luminous flux face upward. One of the hollow cathode lamps 76 required is positioned to a given position by rotating the lamp holder 77. The luminous flux from this hollow cathode lamp 76 is passed through various kinds of optical systems (not illustrated), and is further passed through the graphite furnace analyzing section 3, and the flame analyzing section 4. It finally reaches to a photomultiplier, and is converted into an electric signal. After that, a personal computer (not illustrated) placed next to the main unit 1 executes the quantitative analysis of target metal. With the door 21 of the lamp chamber 2 being opened, the hollow cathode lamp 76 is replaced.

The cooling drain pot 8, which is used for coolant such as water for cooling units inside the atomic absorption spectrophotometer, is provided on the left surface of the main unit 1.

In the atomic absorption spectrophotometer according to the prior art as described above, the plural hollow cathode lamps 76 (in the case of the example shown in FIG. 14, eight hollow cathode lamps 76) are attached to the lamp holder 77 that is rotatable. Positioning one of them to a given position makes it possible to analyze metal corresponding to the positioned lamp. Accordingly, it is possible to analyze eight kinds of metals successively and continuously without replacing the lamps. Moreover, it becomes possible to analyze many kinds of metals by replacing the hollow cathode lamps 76.

Incidentally, the prior art relating to the atomic absorption spectrophotometer as described above is known, for example, by the technology described in Japanese Patent Application Laid-Open No. Hei 10-73536, and others.

The atomic absorption spectrophotometer according to the prior art is configured as a tandem machine comprising the flame analyzing section and the graphite furnace analyzing section. In addition, the power unit, and the like, is placed behind the analyzing sections. Therefore, since its width and depth are large, a large area for installing the spectrophotometer has been required.

In addition, as for the above-mentioned prior art, if a special-purpose machine having only either the flame analyzing section or the graphite furnace analyzing section is required, the special-purpose machine is configured by utilizing the main unit that can be used in common. In this case, an unnecessary analyzing section is covered by a lid, or the like. Therefore, even if the Spectrophotometer is used as a special-purpose machine for flame analysis or a special-purpose machine for graphite furnace analysis, its dimensions cannot be reduced. Accordingly, if the machine is placed on the laboratory table in a laboratory, or the like, it protrudes from there.

Moreover, if an atomic absorption spectrophotometer comprising a graphite furnace analyzing section is configured, it is necessary to inject a sample into an atomization furnace with accuracy. In this case, as a general rule, the sample injection is automated by the autosampler. However, the atomic absorption spectrophotometer according to the prior art uses an autosampler of the rotary method that is difficult to adjust. Further, the autosampler protrudes forward from the front surface of the atomic absorption spectrophotometer. Therefore, when placing the atomic absorption spectrophotometer on a table, there is a high possibility that the autosampler will extend off the table into a passageway. Thereby, it is possible that people or something carelessly hit or touch the autosampler requiring a high degree of accuracy. Furthermore, because the autosampler is often placed in the front part of the graphite furnace, the autosampler becomes an obstacle to maintenance of the graphite furnace, making it difficult to perform maintenance work.

SUMMARY OF THE INVENTION

The object of the present invention is to provide an atomic absorption spectrophotometer that can reduce its installed area, that comprises an autosampler with a high degree of accuracy, adjustment of which is easy, and that can make the maintenance work easy.

The present invention is configured as follows to achieve the above-mentioned object.

The atomic absorption spectrophotometer comprises a graphite furnace analyzing section and a lamp chamber for hollow cathode lamps, which are placed in the same main unit, or further comprises a flame analyzing section. Wherein an autosampler having a quadrangular sample tray is placed on the top of the lamp chamber.

In addition, the following configuration is proposed to achieve the above object. The atomic absorption spectrophotometer comprises a housing section for transformer and power supply unit. The housing section is placed behind the main unit. A power unit for supplying electric power required for the whole atomic absorption spectrophotometer, is placed at the lower part of the housing section. A control circuit board for controlling the whole atomic absorption spectrophotometer is placed at the upper part of the housing section. And a door is provided on the front of the graphite furnace analyzing section. The door allows maintenance inside the graphite furnace analyzing section to be performed from the front side of the atomic absorption spectrophotometer.

In the above description, a large number of sample bottles are arranged into an array lengthwise and crosswise on the quadrangular sample tray, and plural reagent bottles are aligned along the innermost side of the sample tray. The autosampler drives an arm for holding an aspiration needle in the lateral direction, and drives the sample tray in the depth direction, so as to select a sample.

BRIEF DESCRIPTION OF THE DRAWINGS

FIG. 6 is a diagram illustrating an example of an optical path of a light beam emitted from a hollow cathode lamp;

FIGS. 7A, 7B, 7C are diagrams illustrating a configuration of an autosampler;

FIGS. 8A, 8B, 8C are exploded perspective views illustrating a configuration of a sample tray;

FIGS. 9A, 9B, 9C are plane views illustrating sample trays including an adapter for microplate;

DESCRIPTION OF THE PREFERRED EMBODIMENTS

Embodiments of an atomic absorption spectrophotometer according to the present invention will be described in detail with reference to drawings as below.

Figure 1A:
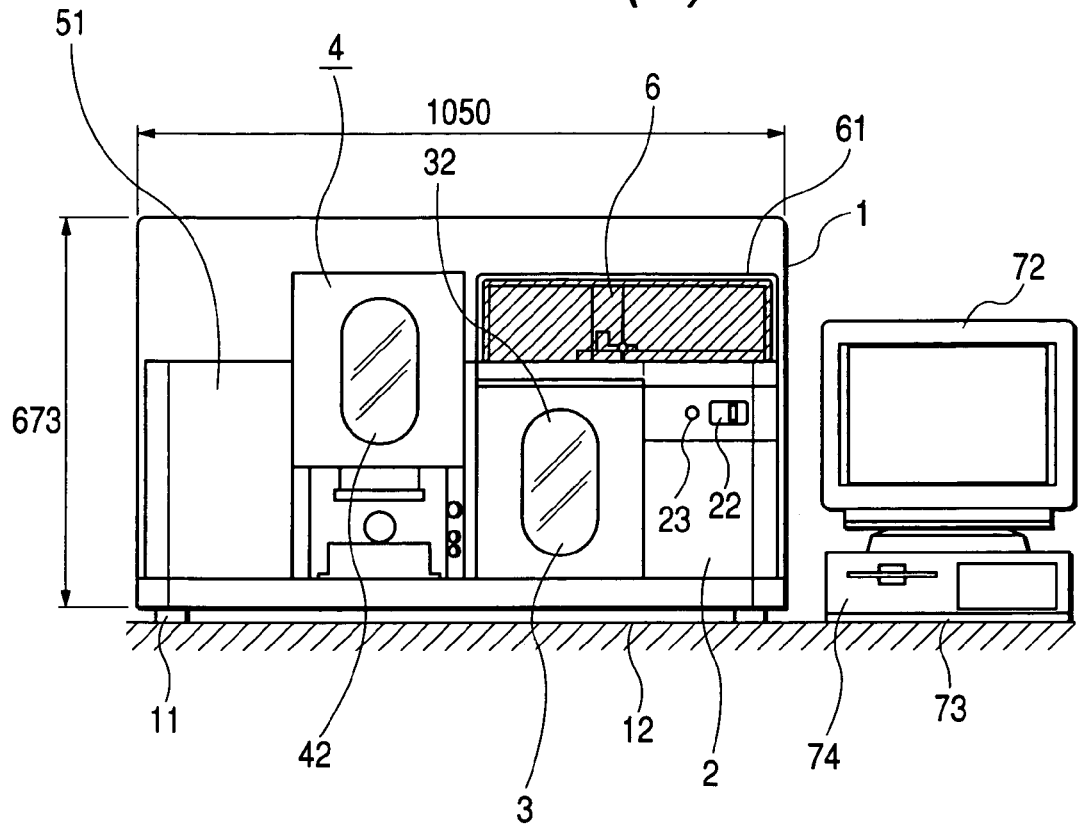
FIGS. 1A and 1B are front and side views illustrating a shape of an atomic absorption spectrophotometer according to a first embodiment of the present invention.
Figure 1B:
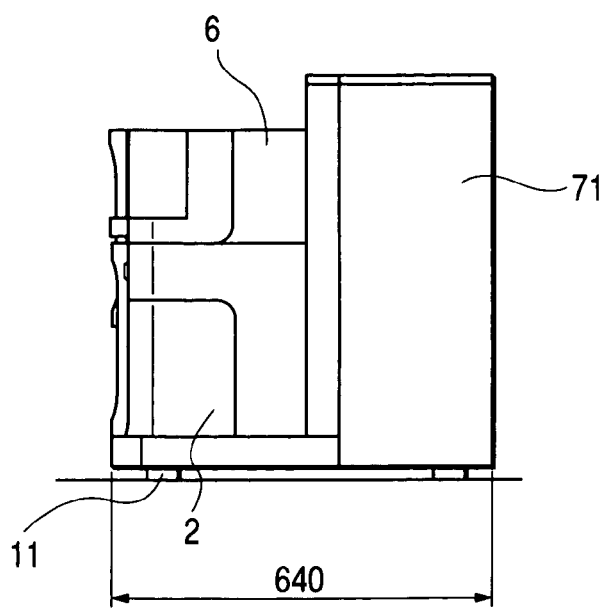
Figure 2:
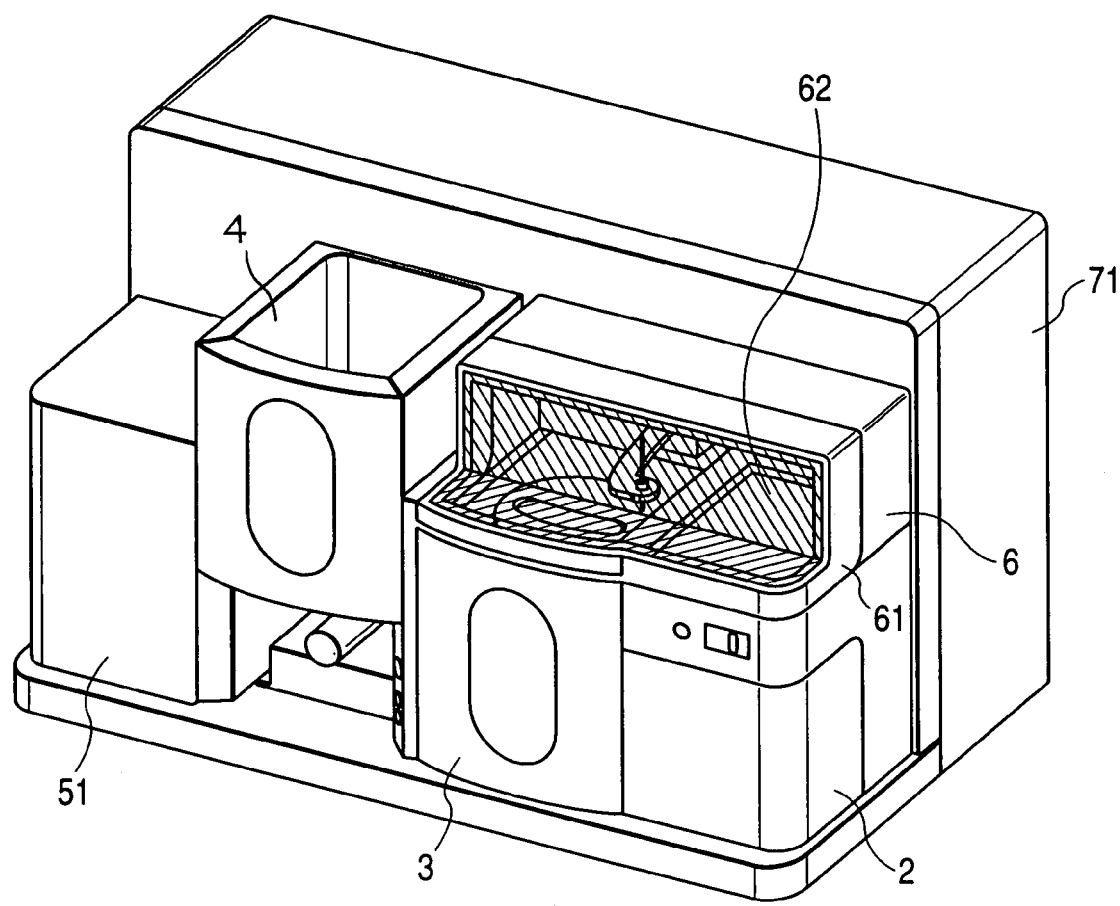
FIG. 2 is a perspective view illustrating the appearance of the atomic absorption spectrophotometer according to the first embodiment of the present invention.
Figure 3:
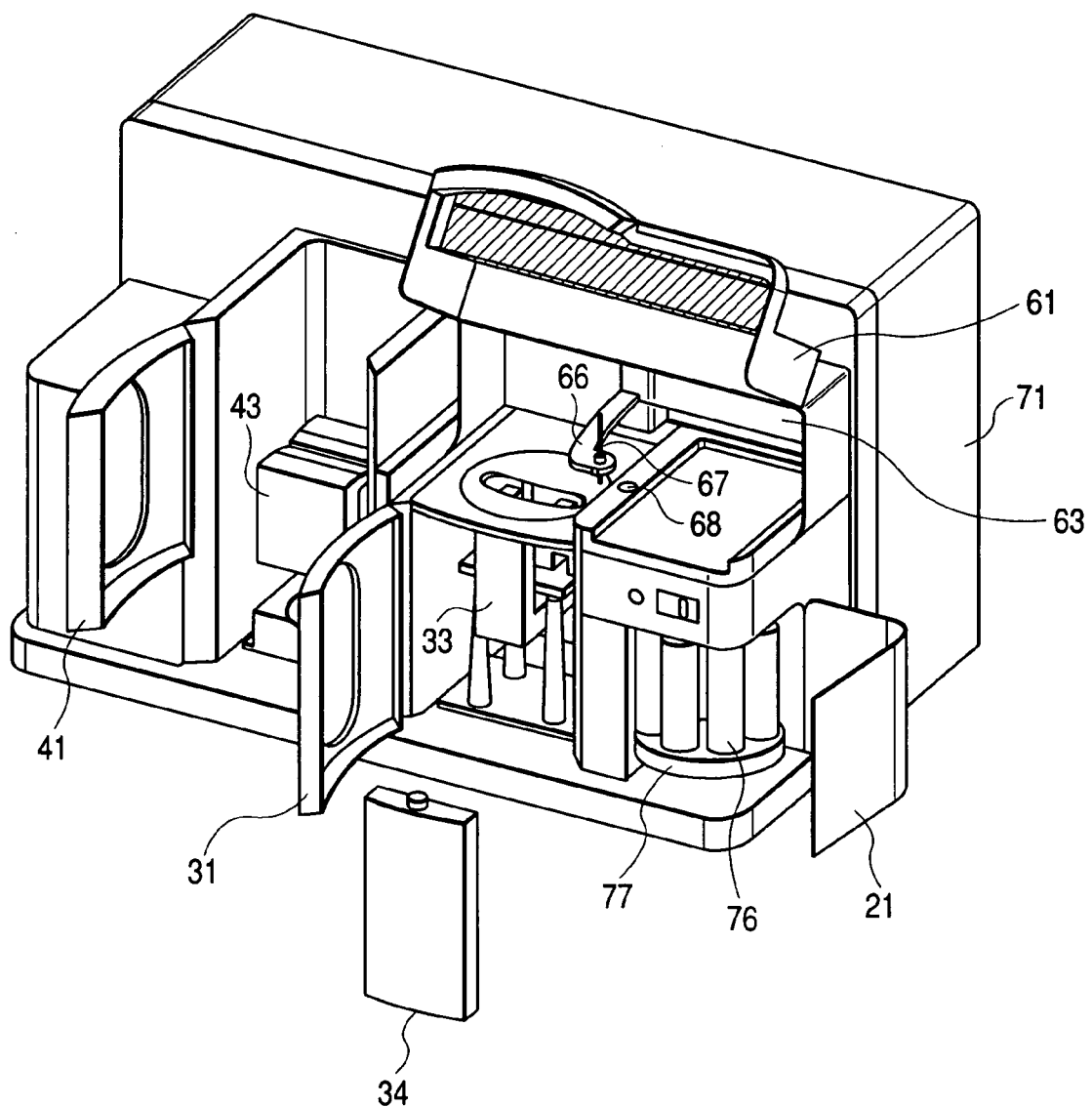
FIG. 3 is a perspective view illustrating the atomic absorption spectrophotometer shown in FIG. 2, which is in a state in which its door is opened.
Figure 4:
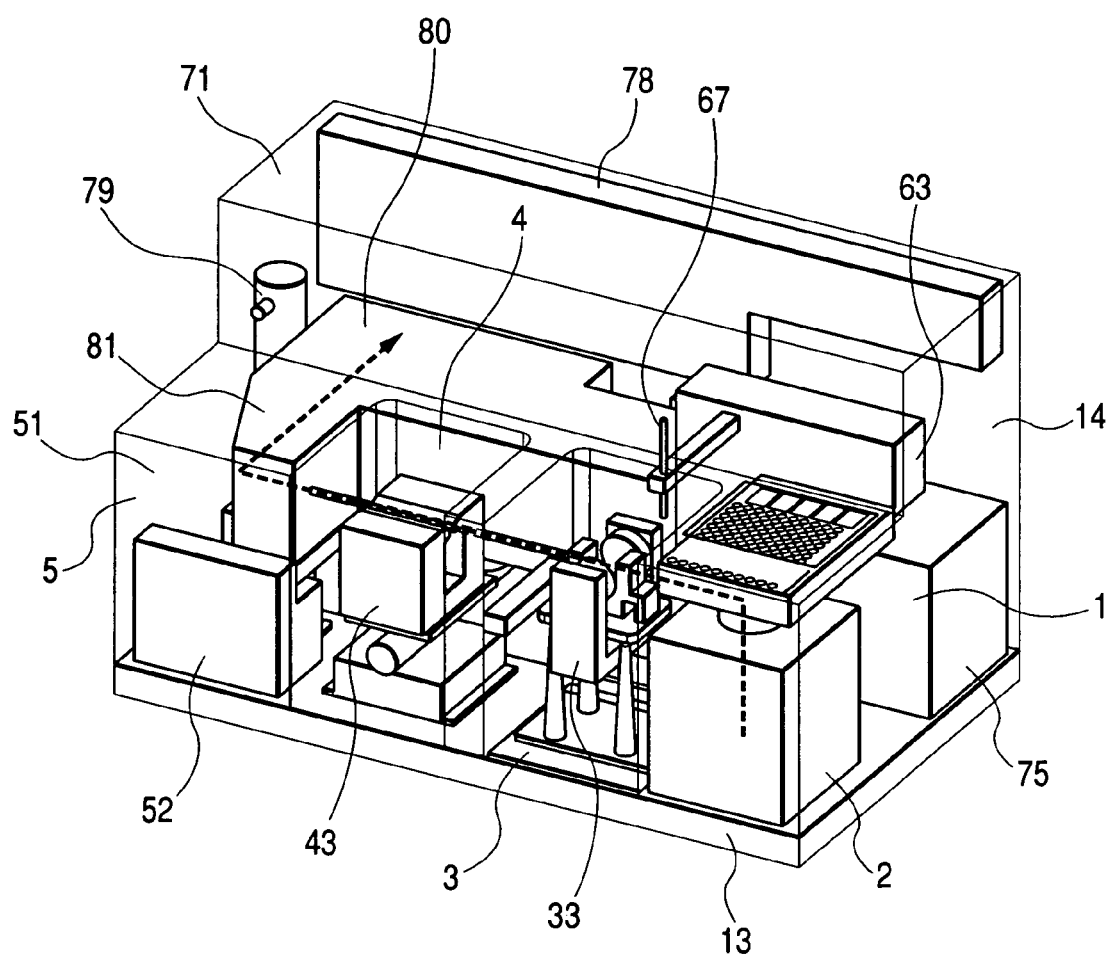
FIG. 4 is a drawing illustrating the inside of the atomic absorption spectrophotometer from which doors provided on the front side of a main unit, and side walls forming sides of the main unit, are excluded.
Figure 13:
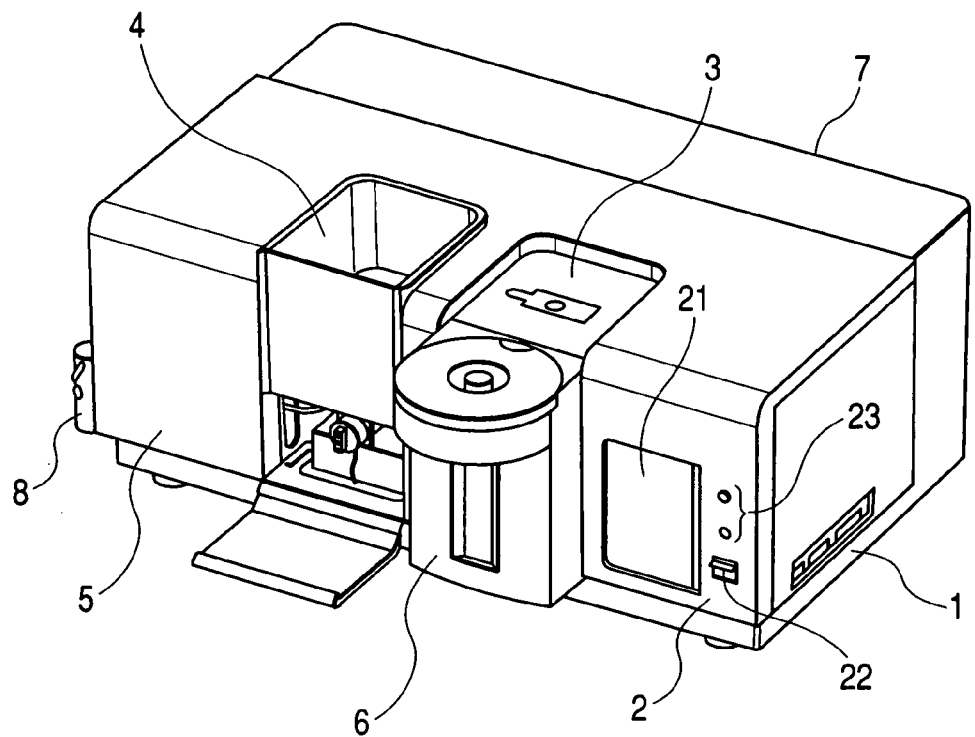
FIG. 13 is a perspective view illustrating a configuration of an atomic absorption spectrophotometer according to the prior art.
Figure 14:
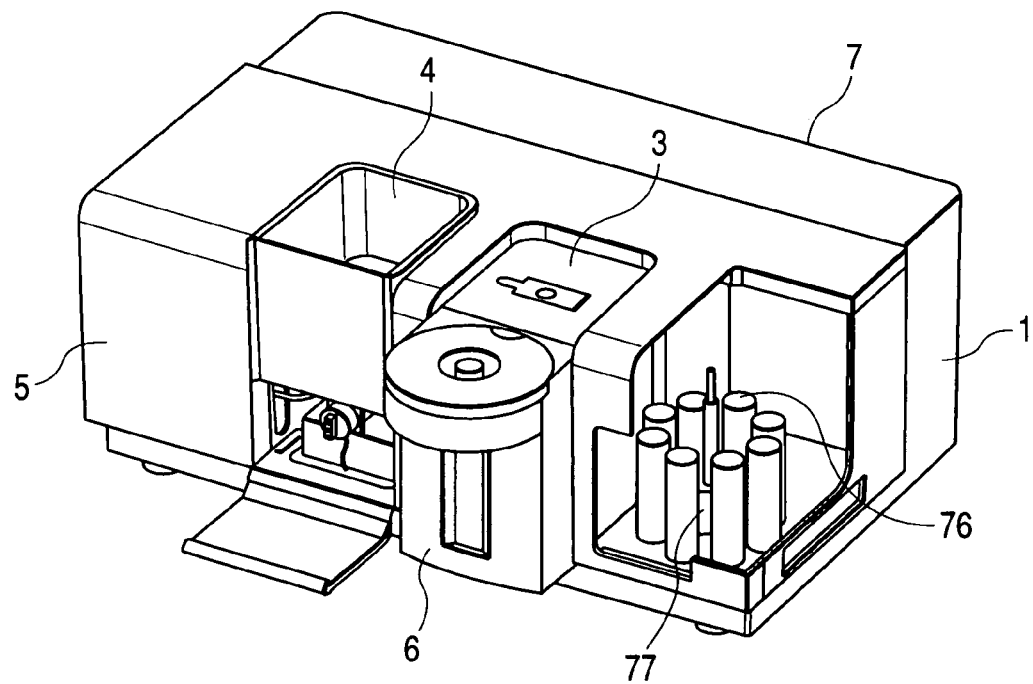
FIG. 14 is a diagram illustrating a state inside a lamp chamber.

FIGS. 1A and 1B are front and side views illustrating a shape of an atomic absorption spectrophotometer according to a first embodiment of the present invention. FIG. 2 is a perspective view illustrating the appearance of the atomic absorption spectrophotometer according to the first embodiment of the present invention. FIG. 3 is a perspective view illustrating the atomic absorption spectrophotometer shown in FIG. 2, which is in a state where its door is opened. FIG. 4 is a drawing illustrating the inside of the atomic absorption spectrophotometer from which doors provided on the front side of a main unit, and side walls forming sides of the main unit, are excluded. In FIGS. 1 through 4, reference numeral 11 denotes feet; reference numeral 12 denotes a table; reference numerals 31, 41 denote doors; reference numerals 32, 42, 62 denote clear windows; reference numeral 51 denotes a housing section for flame gas controller; reference numeral 52 denotes a flame gas controller; reference numeral 61 denotes a dust-preventive cover; reference numeral 63 denotes an autosampler controller; reference numeral 71 denotes a housing section for transformer and power supply unit; reference numeral 72 denotes a display; reference numeral 73 denotes a keyboard; reference numeral 74 denotes a personal computer; reference numeral 75 denotes a power unit; reference numeral 78 denotes a space for circuit board; and reference numeral 79 denotes an air filter. The other reference numerals correspond to the same reference numerals of FIGS. 13, 14.

The first embodiment of the present invention shown in FIGS. 1 through 4 is an example of an atomic absorption spectrophotometer having a tandem type configuration, which comprises both the graphite furnace analyzing section 3 and the flame analyzing section 4. As illustrated in the front view of FIG. 1A, the lamp chamber 2, the graphite furnace analyzing section 3, the flame analyzing section 4, and the flame gas controller 51 are sequentially placed from right to left inside the main unit 1. In addition, the autosampler 6 is placed on the top of the lamp chamber 2. Further, the housing section 71 for transformer and power supply unit is used as the space for the power unit 75, and used as the space 78 for the circuit board etc. The housing section 71 is placed behind the lamp chamber 2, the graphite furnace analyzing section 3, the flame analyzing section 4, and the flame gas controller 51. The power unit 75 supplies electric power required for the whole atomic absorption spectrophotometer as well as the graphite furnace analyzing section 3. The control circuit board is used for controlling the whole atomic absorption spectrophotometer.

The bottom surface of the main unit 1 is equipped with the feet 11 for absorbing vibrations, and the whole atomic absorption spectrophotometer of the first embodiment of the present invention is placed on the table 12, or the like through the feet 11. In addition, the personal computer 74 having the display 72 and the keyboard 73, which is used for controlling and operating the whole atomic absorption spectrophotometer, is placed on the table 12. As shown in FIG. 4, the power unit 75 which includes a graphite furnace heating transformer for supplying electric power to the graphite furnace, is provided at the lower part of the housing section 71 for transformer and power supply unit. The space 78 for circuit board is provided at the upper part of the housing section 71 for transformer and power supply unit, and the control circuit board is put in the space 78.

As shown in the side view in FIG. 1B and the perspective view in FIG. 2, the whole atomic absorption spectrophotometer of the first embodiment of the present invention is formed as follows. The housing section 71 for transformer and power supply unit, which is provided behind the lamp chamber 2, the graphite furnace analyzing section 3, the flame analyzing section 4, and the flame gas controller 51, is formed higher than the other sections. And the whole shape of the spectrophotometer viewed from the side is formed in a rough L-shape. Thus, since the housing section 71 can house the control circuit board, the power unit, and the like, from top to bottom with taking advantage of the height of itself. It is possible to reduce a thickness of the housing section 71 for transformer and power supply unit, thereby the depth of the whole atomic absorption spectrophotometer can be reduced.

Additionally, in the above-mentioned embodiment of the present invention, the autosampler is placed using a step shape on the top front surface of the main unit, which is formed by adopting a rough L-shape as the side shape. That is, in this embodiment, a sample tray 65 is placed on a flat surface formed on the top of the lamp chamber 2 adjacent to the graphite furnace analyzing section 3; and an X-axis driving mechanics 69 (shown in FIG. 7(a) through to FIG. (b)) of an arm 66 used for injecting a sample into the sample tray is provided at a front vertical plane of the housing section 71 for transformer and power supply unit, which is placed behind the lamp chamber 2 and the graphite furnace analyzing section 3. As a result, it is possible to efficiently house a Y-axis driving mechanics 651 (shown in FIG. 7 (c)) in the lower part of the sample tray 65, and to efficiently house the X-axis driving mechanics 69 inside the housing section 71 for transformer and power supply unit protruding upward. In addition, it is also possible to keep the moving space of the arm 66.

In the above embodiment of the invention, a plurality of hollow cathode lamps 76 attached to a turret-type lamp holder 77 are placed in the lamp chamber 2 in the same way as the prior arts. The hollow cathode lamps 76 are attached to the lamp holder 77 perpendicularly, that is to say, in a vertical direction so that the hollow cathode lamps 76 are replaceable and their emission surfaces of luminous flux face upward. One of the hollow cathode lamps 76 required is positioned to a given position by rotating the lamp holder 77. As described below, the luminous flux from this hollow cathode lamp 76 is passed through various kinds of optical systems, and is further passed through the graphite furnace analyzing section 3 and the flame analyzing section 4. And the luminous flux reaches finally to a photomultiplier, it is converted into an electric signal there. After that, the personal computer 74 placed next to the main unit 1 executes the quantitative analysis of target metal. The replacement of the hollow cathode lamps 76 are done by opening the door 21 of the lamp chamber 2.

The door 21 of the lamp chamber 2 is formed into a bent lid shape that extends to both the front and the side of this lamp chamber 2. Accordingly, the door 21 can be widely opened from the front toward the side of the lamp chamber 2 by use of a hinge mechanism provided on the side (not illustrated). Therefore, it is possible to easily replace the plurality of lamps 76 that are arranged on the circle shaped lamp holder 77 placed in the lamp chamber 2.

As shown in FIG. 3, doors 31, 41 are provided at the front of the graphite furnace analyzing section 3 and at the front of the flame analyzing section 4 respectively. These doors 31, 41 can be opened when performing maintenance such as cleaning. In addition, the doors 31, 41 are provided with clear windows 32, 42 respectively, through which an operation state of each section can be checked. Moreover, although it is not illustrated, the door 21 of the lamp chamber 2 may also be provided with a similar window. It is desirable that in order to protect eyes of an operator, these windows be made of a material which do not allow ultraviolet ray and infrared ray to pass through, including smoke glass, or made of punching metal, or the like.

A detailed configuration of the autosampler 6 placed on the top of both the lamp chamber 2 and the graphite furnace analyzing section 3 will be described later. The autosampler 6 used in the embodiment of the invention, supplies the sample into the graphite furnace as follows instead of the rotary method in which adjustment of the sample supply positions is difficult. The adjustment is performed by the position control of x, y, and z axial direction, which is accurately and easily adjustable. As shown in FIG. 4, the autosampler controller 63 which performs the above-mentioned control in X, Y, and Z directions is housed in the housing section 71 for transformer and power supply unit. As shown in FIGS. 2 and 3, the dust-preventive cover 61 which can be opened and closed is provided on the top of the autosampler 6. The dust-preventive cover 61 has the clear window 62 through which an internal state can be checked easily. The dust-with preventive cover 61 comprises a rough L-shaped flame equipped with clear window 62 in the center.

To be more specific, in the embodiment of the present invention, forming the side of the main unit 1 into a rough L-shape produces a step (concave portion) on the top front of the main unit 1. Accordingly, using this step (concave portion), it is possible to make the moving space for the arm 66 of the autosampler 6 so as not to protrude beyond a projected area of the main unit 1. The whole atomic absorption spectrophotometer, therefore, can be configured to be compact. In addition, as the whole autosampler 6 is covered by the dust-preventive cover 61, it is possible to prevent dust from entering at the time of sample extraction, which enables improvement in accuracy of measurement.

Moreover, the upper part of the flame analyzing section 4 is formed into a chimney shape, the height of which is higher than those of the graphite furnace analyzing sections 3 and the lamp chamber 2. Because the dust-preventive cover 61 is placed using this height difference, it is possible to design so that both heights of the upper end surface of the flame analyzing section 4 and the upper end surface of the dust-preventive cover 61 are rough same. Thereby the whole design of the spectrophotometer is improved.

Moreover, as shown in FIG. 3, in this embodiment, the whole autosampler 6 is not covered only by the dust-preventive cover 61 which can be opened and closed but is covered by the support member for the cover 61. The support member is fixed behind the dust-preventive cover 61, and the cover 61 is attached at front edge of the support member part through its pivot. As a result, the dust-preventive cover 61 can be made small enough without sacrificing workability, which thereby facilitates opening and closing of the dust-preventive cover 61.

As shown in FIG. 4, the graphite furnace analyzing section 3 is equipped with a graphite furnace 33, and the flame analyzing section 4 is equipped with a burner 43. Because these are conventionally well-known configurations, their detailed descriptions will be omitted here. In addition, a cleaning bottle 34, which stores cleaning liquid used clean an aspiration needle for absorbing samples of the autosampler 6, is placed next to the graphite furnace 33 in the graphite furnace analyzing section 3. FIG. 3 illustrates the cleaning bottle 34 in a state of being taken out from the graphite furnace analyzing section 3.

In the embodiment of the invention, the cleaning bottle 34 can be attached inside the door 31. Thus, the space for placing the cleaning bottle 34 is gotten. And the configuration also makes it possible to check the quantity of liquid in the cleaning bottle 34 through the window 32 of this door 31. Because the graphite furnace 33 which is an electric furnace is brighter than the burner 43 that is a gas furnace, the graphite furnace analyzing section 33 does not usually provided with the window 32. However, in this embodiment, the window 32 is provides at the graphite furnace analyzing section 3 so that the quantity of liquid in the cleaning bottle 34 placed between the graphite furnace 33 and the door 31 can be checked.

Then, in this embodiment, as shown by a heavy line in FIG. 4, the luminous flux from the lamp 77 of the lamp chamber 2 passes through analytic centers of the graphite furnace analyzing section 3 and the flame analyzing section 4 in a straight line. The luminous flux is reflected by a mirror (not shown) in a spectral unit 80, and travels toward the back side of the main unit 1, finally is inputted into a spectroscope provided in the housing section 71. The end of the spectral unit 80 is on the top of the flame gas controller 52.

In the embodiment, an optical part including the spectroscope and a photomultiplier PMT is constituted of a single spectral unit 80. The spectral unit 80 is formed as a box body having a thin box-shape, which partially protrudes forward, and the top surface of which has a rough L-shape. In the embodiment, as mentioned above, the protruding part 81 of the spectral unit 80 is on the top of the flame gas controller 52, and a main body of the unit 80 is in the housing section 71 for transformer and power supply unit. The result in consideration of the positional relationship among the lamp 76, the graphite furnace 33, and the burner 43, the spectrophotometer is designed so that the luminous flux indicated by the heavy line in FIG. 4 is pass through, in a straight line, above the lamp chamber 2, the graphite furnace analyzing section 3, the flame analyzing section 4, and the electric control section 5. Corresponding to this, the protruding part of the spectral unit 80, which receives the luminous flux, is placed on the top of the flame gas controller 52. Using this positional relationship, the flame gas controller 52 is placed in the lower part inside the housing section 51 for flame gas controller to improve mounting efficiency.

The rear part of the spectral unit 80 is placed in the middle position of the housing section 71 for transformer and power supply unit. As the spectral unit 80 requires the accuracy, the spectral unit is supported on a bottom panel 13 or the side panel 14 shown in FIG. 5A by supporting means (not illustrated).

Moreover, in FIG. 4, as a result of placing the spectral unit 80 in the middle position, the inside of the housing section 71 for transformer and power supply unit is divided into upper and lower areas. The divided upper and lower areas are used in the following manner: the upper area is used as the space 78 for circuit board that stores a control circuit board, and also as space for storing the autosampler controller 63; and the lower area is used as space for placing various kinds of internally mounted parts. The heavy internal units such as the power unit 75 are placed on the bottom panel 13, thereby the unit can be stably installed. Accordingly, the power unit 75 placed in the lower part described above. Moreover, if a large power unit 75 is used, it is desirable to place it behind the lamp chamber 2 like the embodiment. In the embodiment, as the length of the spectral unit 80 in lateral direction is shorter than the breadth of the main unit 1, some space which is not interrupted by the spectral unit is left behind the lamp chamber 2. The power unit 75 which is tall comparatively is placed in this space.

Additionally, in this embodiment, the driving mechanism of the autosampler 6 such as the X-axis driving mechanics 69 and others, are placed on one side of the storing space provided above the analysis unit 80. The control circuit board in space 78 for circuit board is placed on the other side of above storing space. And they are arranged in parallel backward and forward. As a result, by removing exterior parts of the housing section 71 for transformer and power supply unit, the internal maintenance of the housing section 71 can be performed easily.

As shown in FIG. 4, in the back position of the space 51 for the flame gas controller in the housing section 71 for transformer and power supply unit, the air filter 79, which is used for removing dust when taking in air for gas combustion, is provided.

As shown in FIG. 1A, the atomic absorption spectrophotometer of this embodiment has the following sizes for example: a width is 1050 mm; a depth is 640 mm; and a height is 673 mm. The atomic absorption spectrophotometer can be placed on a table, or the like, through the feet 11 in a stable state, and can be used thereon.

Moreover, in the above-mentioned embodiment of the invention, the main unit 1 comprises a front cabinet which is short, and a rear cabinet which is tall. The lamp chamber 2 and the flame gas controller 52 are placed on both sides of the front cabinet. The analyzing sections are placed between the lamp chamber 2 and the flame gas controller 52. The housing section 71 for transformer and power supply unit is configured with the rear cabinet. The driving mechanism of the autosampler 6, the power unit, the control circuit board, and the like, are placed in the housing section for transformer and power supply unit. In this embodiment, the graphite furnace analyzing section 3 and the flame analyzing section 4 are placed as the above-mentioned analyzing sections. The luminous flux from the lamp chamber 2 travels up to the flame gas controller 52. The spectral unit 80 is placed in an area including the upper part of the flame gas controller 52 and the middle position of the housing section 71 for transformer and power supply unit. The above-mentioned luminous flux is introduced into the spectral unit 80. The space 78 for circuit board and the autosampler controller 63 are placed above the spectral unit 80. The power unit 75 which is a heavy unit is placed in the lower part. In this embodiment, a compact atomic absorption spectrophotometer is realized by placing the sample tray 65, and the arm 66, of the autosampler 6 in the step formed by both the top of the front cabinet and the upper front of the rear cabinet that stands up behind the top of the front cabinet.

Figure 5A:
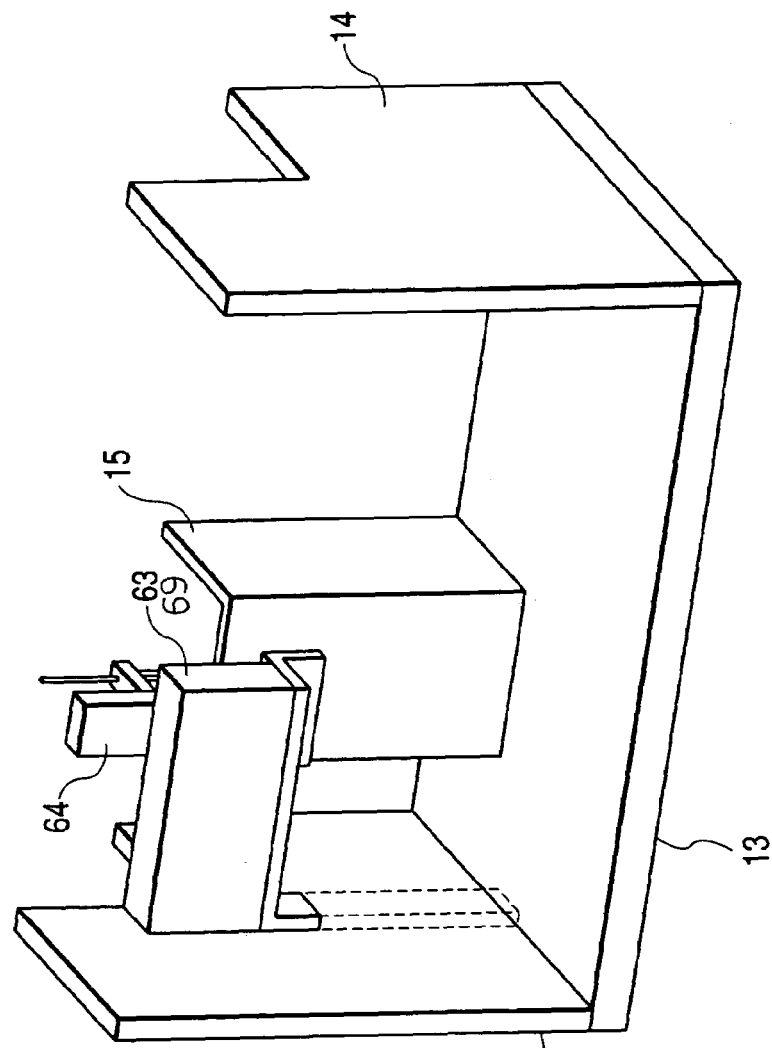
FIGS. 5A, 5B, 5C are perspective views illustrating a configuration of the main unit according to the embodiment of the present invention, which is viewed from the back.
Figure 5B:
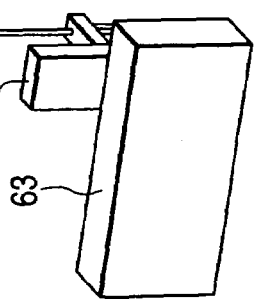
Figure 5C:
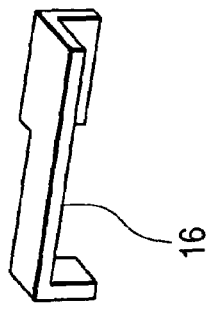

FIGS. 5A, 5B, 5C are perspective views illustrating a configuration of the decomposed main unit 1 according to the embodiment of the present invention, which is viewed from the back. Next, the main unit 1 will be described. For the purpose of describing its internal structure, the figure shown here illustrates a state in which a back plate covering the back of the atomic absorption spectrophotometer is removed. In FIGS. 5A, 5B, 5C, reference numeral 13 denotes the bottom panel; reference numerals 14 denote the side panels; reference numeral 15 denotes a division of graphite furnace; reference numeral 16 denotes an autosampler controller loading chassis; and reference numeral 64 denotes a Z-axis driving mechanics.

As shown in FIG. 5A, the main unit 1 comprises the following: the bottom panel 13; the side panels 14 connected to the bottom panel 13 at right and left ends; and a back panel (not illustrated). In a part inside the main unit 1 where the graphite furnace analyzing section 3 is placed, the division 15 of graphite furnace. The division 15 has a square U-shape wall so as to surround the graphite furnace analyzing section 3, and that is placed in a manner that the opened side corresponds to the front side of the atomic absorption spectrophotometer. The autosampler controller loading chassis 16 having a shape as shown in FIG. 5C, on which the autosampler controller 63 is mounted, is attached between the back surface of the division 15 of graphite furnace and one of the side panels 14, that is the left side when viewing the atomic absorption spectrophotometer from the back.

The division 15 of graphite furnace is provided to intercept the heat from the graphite furnace 33 constituting the graphite furnace analyzing section 3. So the influence of the heat is not exerted upon the other parts of the atomic absorption spectrophotometer.

The atomic absorption spectrophotometer comprises a spectroscope, and a detector. It is necessary to secure them with a high degree of accuracy. For that, the bottom panel 13, the side panel 14, the division 15 of graphite furnace, and the autosampler controller loading chassis 16, which constitute the main unit 1, are made of members with high stiffness, for example, a plate formed by sandwiching a metal corrugated sheet between metal plates from both sides. The division 15 of graphite furnace may be made by containing an insulation material into itself to provide further thermal insulation properties. The autosampler controller loading chassis 16 is fixed to the back surface of the division 15 of graphite furnace, and also to the side panel 14, with bolts and nuts or by welding.

In the example shown in FIGS. 5A, 5C, a joined portion of the autosampler controller loading chassis 16, which is joined to the side panel 14, is formed into a downward short bend shape. However, as indicated with dotted lines in FIG. 5A, a bend-shaped member making up this joined portion can also be formed so that the member reaches the bottom panel 13. This makes it possible to join the autosampler controller loading chassis 16 to the main unit 1 more firmly. As shown in FIG. 5B, the autosampler controller 63 mounted on the autosampler controller loading chassis 16 drives and controls the Z-axis driving mechanics 64 attached to the autosampler controller 63, and thereby selects a specified sample from among a large number of samples placed on the autosampler 6. And then the controller 63 performs control so that the selected sample drops into the graphite furnace analyzing section 3. The operation will be described in detail later.

FIG. 6 is a diagram illustrating an example of an optical path of a light beam emitted from a hollow cathode lamp. Next, this example will be described.

As shown in FIG. 6, luminous flux which is output upward from the hollow cathode lamp 76 is reflected by a mirror M1 in the horizontal direction so as to converge to the center of the graphite furnace analyzing section 3 (GA center). The luminous flux is then condensed to the center of the flame analyzing section 4 (FL center) by a lens L1 provided between the graphite furnace analyzing section 3 and the flame analyzing section 4. After that, the luminous flux is reached to the photomultiplier PMT through mirrors M2 through M7, a prism, and the like. An electric signal from the photomultiplier PMT is inputted into the personal computer where the electric signal is analyzed.

In the above description, the optical path from the mirror M2 up to the photomultiplier PMT may be set flexibility in a manner that the optical path is not interrupted by other units in the main unit 1. In this case, both the center of the graphite furnace analyzing section 3 and the center of the flame analyzing section 4 have only to be placed in an optical path through which a light beam travels in a straight line between the mirror M1 and the mirror M2.

In the case of the above-mentioned example, the mirror M1 is placed on a ceiling of the lamp chamber 2, whereas the mirror M2 is placed on the protruded portion of spectral unit 80 that is above the top of the flame gas controller 52. The part from the mirror M2 up to the photomultiplier PMT is placed in the spectral unit 80.

FIGS. 7A, 7B, 7C are diagrams illustrating a configuration of the autosampler. FIGS. 8A, 8B, 8C are exploded perspective views illustrating a configuration of a sample tray. FIGS. 9A, 9B, 9C are plane views illustrating sample trays including an adapter for microplate. In FIGS. 7 through 9, reference numeral 65 denotes the sample tray; reference numeral 66 denotes an arm; reference numeral 67 denotes an aspiration needle; reference numeral 68 denotes a hole for disposed sample and cleaning; reference numeral 69 denotes an X-axis driving mechanics; reference numeral 651 denotes a Y-axis driving mechanics; reference numeral 652 denotes a sample tray holder; reference numeral 653 denotes a reagent bottle hole; reference numeral 654 denotes a sample bottle hole; reference numeral 655 denotes a reagent bottle; reference numeral 656 denotes a sample bottle; reference numeral 657 denotes a microplate; and reference numeral 658 denotes the adapter for microplate.

As shown in the plane view of FIG. 7A, the autosampler 6 comprises the following: the sample tray 65 on which a large number of the sample bottles 656 and a large number of the reagent bottles 655 are placed; the X-axis driving mechanics 69 provided in the autosampler controller 63, which drives and controls the Z-axis driving mechanics 64 in an X-axis direction (left and right directions when viewing from the front side of the atomic absorption spectrophotometer); the arm 66 mounted on the Z-axis driving mechanics 64, which is driven in the up and down directions by the Z-axis driving mechanics 64; and the aspiration needle 67 mounted on the end of the arm 66, which absorbs a sample and a reagent and then drops them into a cuvette (not illustrated) inside the graphite furnace analyzing section 3. The X-axis driving mechanics 69 and the Z-axis driving mechanics 64, as shown in the plane view in FIG. 7A and the front view in FIG. 7B, are respectively equipped with a drive motor, a belt, etc., and configured by use of the conventionally known technology. Moreover, in the embodiment of the present invention, as shown in the plane view of FIG. 7A, the sample tray 65 can be driven in the Y axial direction, namely, in the depth direction of the atomic absorption spectrophotometer. For this reason, as shown in the side view of FIG. 7C, the Y-axis driving mechanics 651, which is configured in the same manner as the above-mentioned driving mechanics, is provided at in the lower part of the sample tray 65.

In the above description, moving ranges of the arm 66 by the X-axis driving mechanics 69 and the Z-axis driving mechanics 64 are about 320 mm, 90 mm respectively. A moving range of the sample tray 65 by the Y-axis driving mechanics 651 is about 90 mm. The hole 68 for disposed sample and cleaning is provided in an area of the sample tray 65 close to the graphite furnace analyzing section 3.

As a result of configuring the autosampler 6 as described above, the arm 66 having the aspiration needle 67 is driven and controlled only in lateral and longitudinal directions by the X-axis driving mechanics 69 and the Z-axis driving mechanics 64. The sample tray 65 is driven and controlled in the depth direction by the Y-axis driving mechanics 651. Thereby the aspiration needle 67 can be positioned to a given sample bottle 656. It accordingly is possible to perform positioning with a higher degree of accuracy as comparison with the control/driving of the aspiration needle 67 by the conventional triaxial driving.

As shown in FIG. 8A, the sample tray 65 comprises a quadrangular, thick-plate-like member with a large number of the sample bottle holes 654 and plural reagent bottle holes 653. Wherein, the sample bottle holes 654, each of which is cylindrically formed, are arranged into an array lengthwise and crosswise. The reagent bottle holes 653 are aligned along the innermost side of the sample tray 65. The sample bottle 656 and the reagent bottle 655 formed into shapes as shown in FIG. 8C are inserted into the sample bottle hole 654 and the reagent bottle hole 653 respectively. A sample as a specimen is stored in the sample bottle 656; and a sample required for adjusting properties of a reagent is stored in the reagent bottle 655. The sample tray 65 is held on the sample tray holder 652 as shown in FIG. 8B. This sample tray holder 652, together with the sample tray 65, is driven and controlled in the depth direction by the above-mentioned Y-axis driving mechanics 651.

In the above-mentioned example, the sample bottles 656 are arranged into an array within an operating range of the aspiration needle 67. For example, in the case of the example shown in the figure, six sample bottles 656 are aligned in the Y axial direction, and ten sample bottles 656 are aligned in the X axial direction so that they form a grid pattern. The arrangement of the sample bottles 656 is not limited to the illustrated example. If the sample bottles 656 are regularly arranged, they may also be arranged in a punching manner. In this example, the reagent bottles 655 which need the large capacity is respectively formed in a manner that this rectangular bottle has a projecting part on one side. Each projecting part is placed in the same row with the sample bottles 656, and consequently a rectangular part of each reagent bottle 655 is placed out of the operating range of the aspiration needle 67. According to this example, the projecting parts of the reagent bottles 655 and the sample bottles 656 are arranged alternately, and the rectangle parts of the reagent bottles 655 can be arranged at one side of the sample tray. Therefore, it is possible to provide the large amount of reagent without extending the operating range of the aspiration needle 67.

In the above-mentioned example, the sample tray 65 is placed on the top surface of the sample tray holder 652. Accordingly, if how to attach the sample tray 65 to the sample tray holder 652 is standardized (for example, providing protrusions on the top surface of the sample tray holder 652, and providing on the lower part of the sample tray 65 concave portions to fit with the protrusions), the sample tray 65 can also have various kinds of shapes.

FIGS. 9A, 9B, 9C are plane views illustrating sample trays including an adapter for microplate. FIGS. 9A, 9B illustrate examples of the adapter for microplate enabling the use of the microplate 657 that is recently used for genetic research, and the like. Instead of making the sample bottle holes 654 directly on the sample tray 65, the adapter for microplate is formed thereon by making a hole, which can receive the microplate. The hole is on the sample tray 65 made of the quadrangular, thick-plate-like member as described above with reference to FIG. 8A.

The example shown in FIG. 9A is one in which a reagent is not required. In this case, there is no reagent bottle holes 653, there is only a receivable hole at the center of the sample tray 65. The microplate 657 is formed into a quadrangular as one unit in which a large number of concavities for sample, each of which is formed into a shallow, cylindrical shape, are arranged into an array lengthwise and crosswise. The microplate 657 is made of resin, or the like. This microplate 657 is a general-purpose product used for genetic research, and the like. The example shown in FIG. 9B is one in which a reagent is required. In this example, the reagent bottle holes 653 as described in FIG. 8A provided on the sample tray 65, and instead of providing the sample bottle holes 654, the hole receivable the microplate 657 is provided on the sample tray. The example shown in FIG. 9C is the plane view of the sample tray 65 described with reference to FIG. 8A. This example is shown for the purpose of comparing this with FIGS. 9A, 9B. Each portion indicated by a double line in the figures shows a hole into which a reagent bottle is being stored.

Figure 10A:
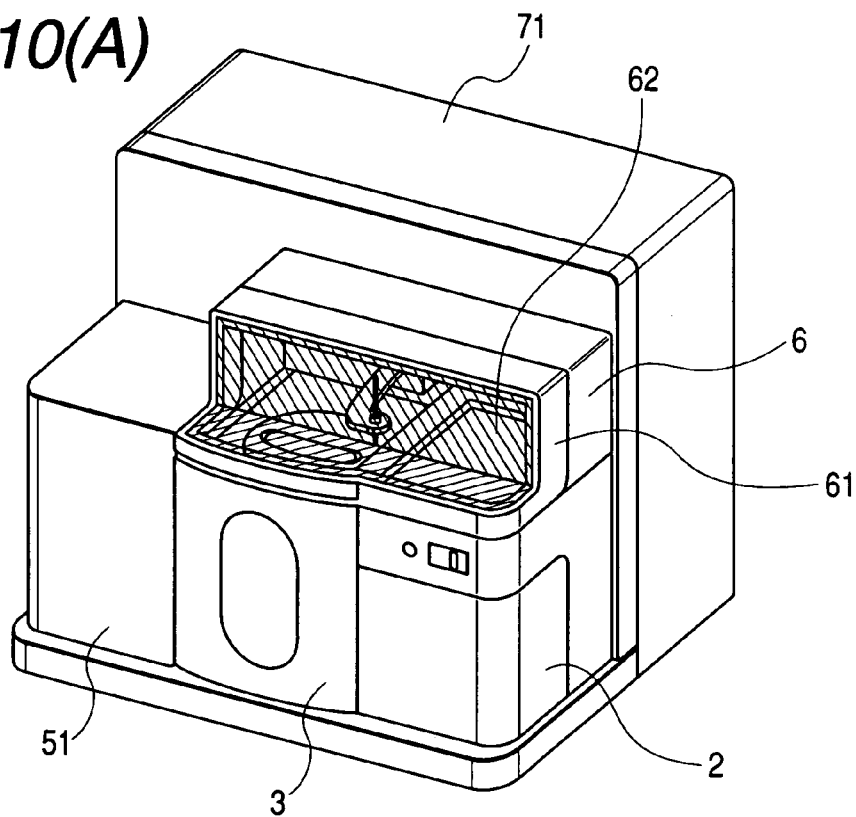
FIGS. 10A, 10B are perspective views illustrating the appearance of an atomic absorption spectrophotometer according to a second embodiment of the present invention.
Figure 10B:
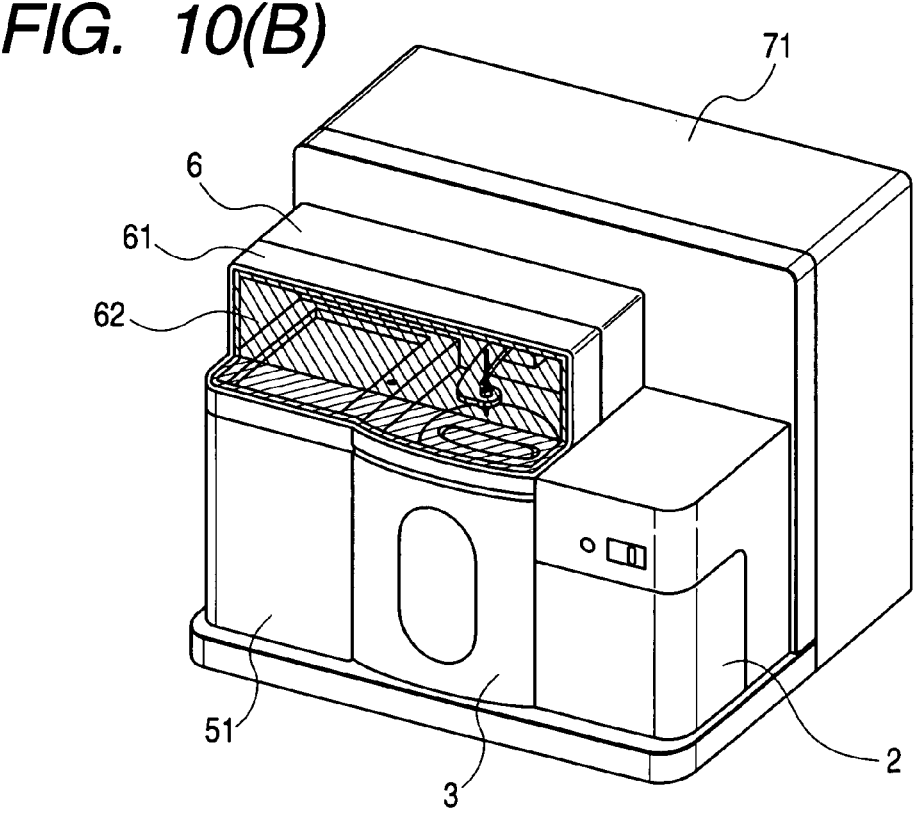
Figure 11:
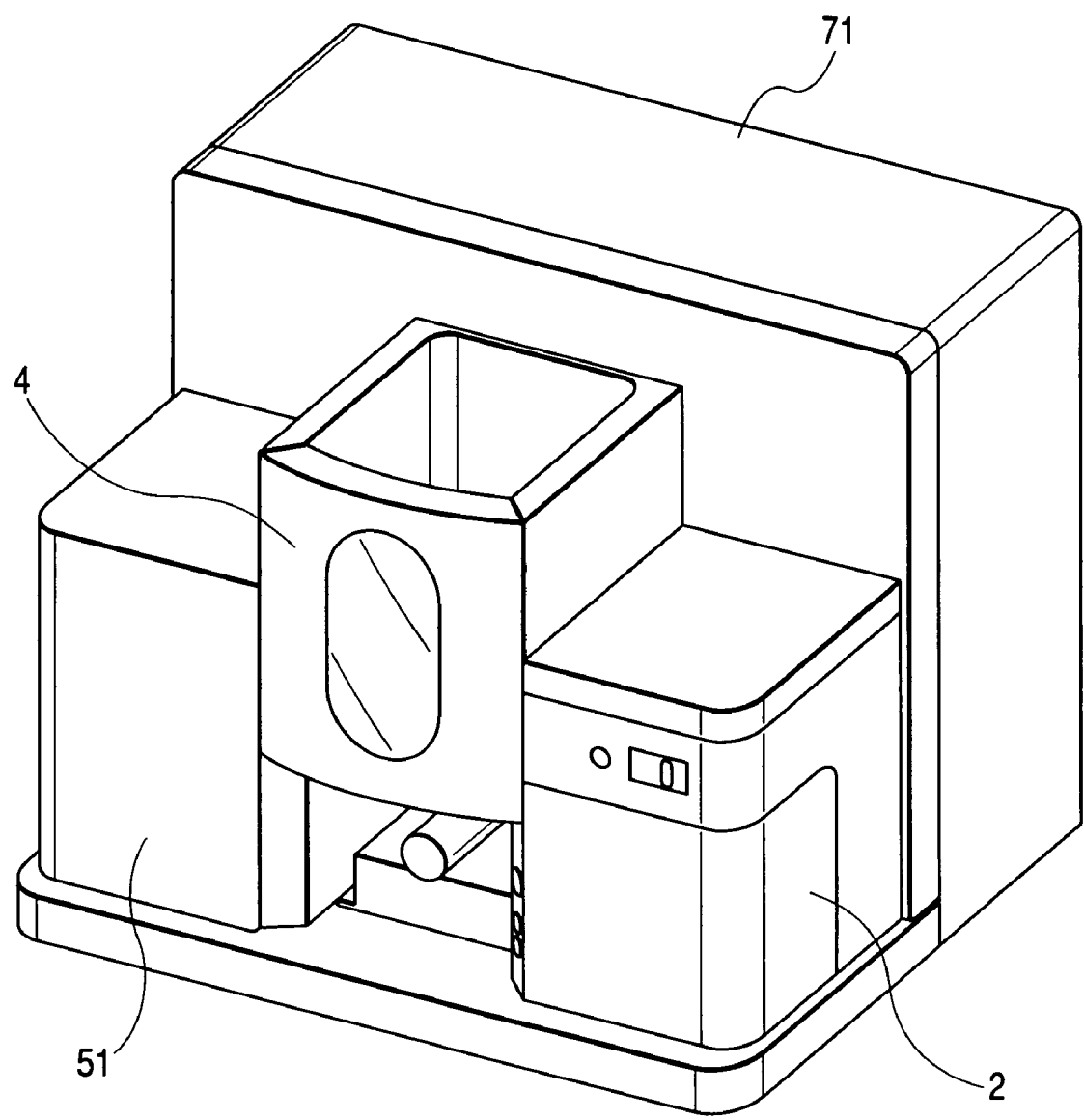
FIG. 11 is a perspective view illustrating the appearance of an atomic absorption spectrophotometer according to a third embodiment of the present invention.

FIGS. 10A, 10B are perspective views illustrating the appearance of an atomic absorption spectrophotometer according to a second embodiment of the present invention. FIG. 11 is a perspective view illustrating the appearance of an atomic absorption spectrophotometer according to a third embodiment of the present invention. Reference numerals used in FIGS. 10, 11 correspond to the same reference numerals of FIG. 2.

The first embodiment of the present invention described above is the example in which both the graphite furnace analyzing section 3 and the flame analyzing section 4 are provided so that they form a tandem type configuration. The second embodiment of the present invention shown in FIGS. 10A, 10B are examples of an apparatus (special-purpose apparatus) used only for graphite furnace analysis, having only the graphite furnace analyzing section 3. The third embodiment of the present invention shown in FIG. 11 is an example of an apparatus used only for flame analysis, having only the flame analyzing section 4.

As shown in FIGS. 10A, 10B, because the second embodiment is configured as the apparatus used only for graphite furnace analysis, this apparatus can be made by excluding the flame analyzing section 4 from the tandem machine according to the first embodiment. Accordingly, it is possible to configure the apparatus used only for graphite furnace analysis narrower than the tandem type configuration by the width occupied by the flame analyzing section 4. The second embodiment includes a configuration example in which the autosampler 6 is placed on the top of the lamp chamber 2 as shown in FIG. 10A, and a configuration example in which the autosampler 6 is placed on the top of the housing section 51 for flame gas controller as shown in FIG. 10B. The second embodiment of the present invention may be any of these configuration examples. In a similar manner, as shown in FIG. 11, because the third embodiment of the present invention is configured as the apparatus used only for flame analysis, this apparatus can be made by excluding the graphite furnace analyzing section 3 from the tandem machine according to the first embodiment. Accordingly, it is possible to configure the apparatus used only for flame analysis narrower than the tandem type configuration by the width occupied by the graphite furnace analyzing section 3.

The main units according to the second and third embodiments have only to provide internal space for housing only internal units required as the special-purpose apparatuses. Even if the main units are designed narrower than that of the tandem machine by the width described above, the main unit can sufficiently house the internal units. Additionally, in the second and third embodiments, the special-purpose machines are so devised that the depth of the main unit 1 is the same as that of the tandem machine. Therefore, it is possible to provide commonality of the greater part of structural members constituting the main unit 1 across the special-purpose machines and the tandem machine, and thereby costs can be reduced.

Incidentally, the second embodiment of the present invention describes both the example in which the autosampler 6 is placed on the top of the lamp chamber 2, and the example in which the autosampler 6 is placed on the top of the housing section 52 for the flame gas controller 52. In any case, it is possible to produce the same effects as the first embodiment.

Figure 12A:
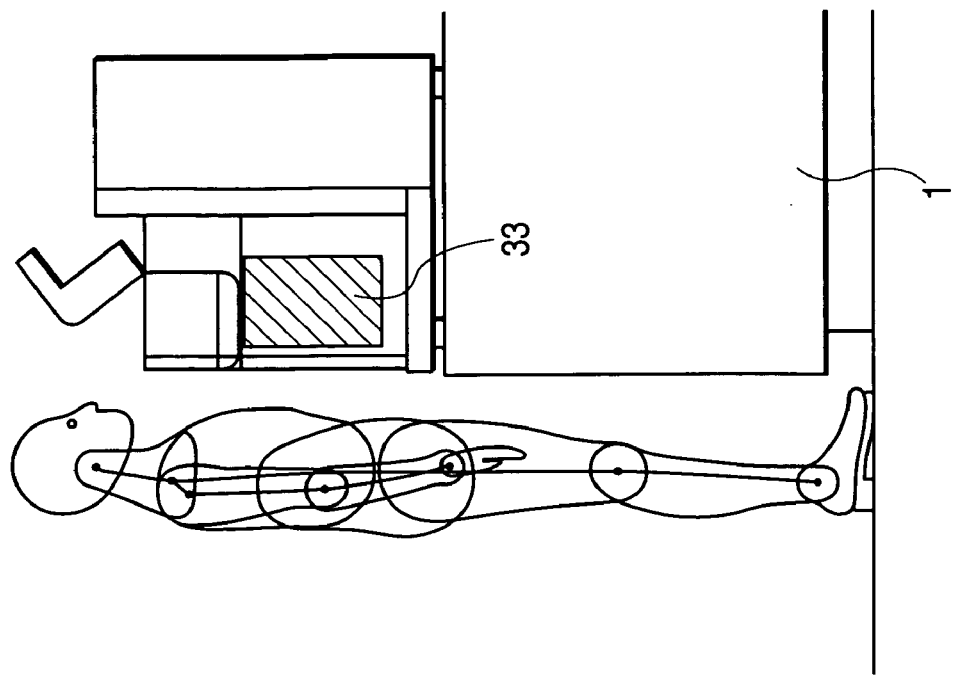
FIGS. 12A, 12B are diagrams illustrating situations at the time of maintenance.
Figure 12B:
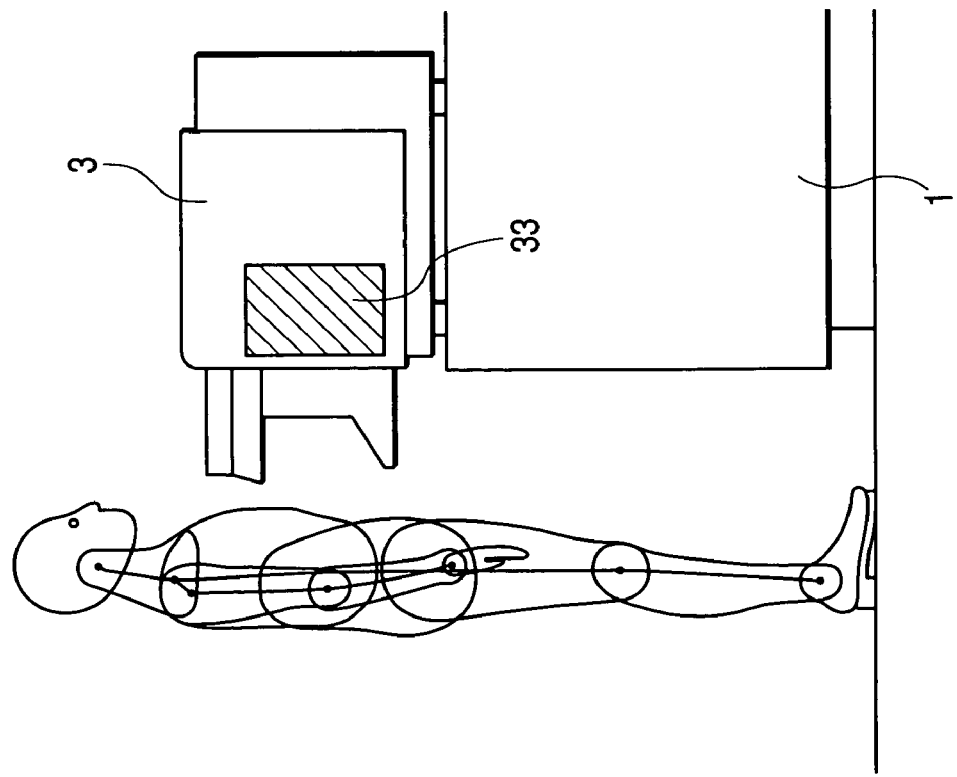

FIGS. 12A, 12B are diagrams illustrating situations at the time of maintenance. Next, how maintenance can be facilitated in each of the embodiments of the invention will be described with reference to FIGS. 12A, 12B.

FIG. 12A illustrates a situation for the prior art. In the case of the prior art, as described previously, the autosampler using the rotary method is placed in the front part of the graphite furnace analyzing section 3, and consequently the autosampler protrudes forward from the main unit 1. Therefore, it is difficult to perform maintenance of the graphite furnace constituting the graphite furnace analyzing section 3, for example, maintenance work such as cleaning, and replacement, of a cuvette stored in the graphite furnace, because the maintenance work is impeded by the autosampler.

On the other hand, in the case of the embodiments according to the invention, because the autosampler is formed into a quadrangle and is placed on the lamp chamber, the autosampler does not protrude forward from the main unit 1. Accordingly, only opening the door of the graphite furnace analyzing section 3 enables easy maintenance of the graphite furnace from the front side.

According to each embodiment described above, because the autosampler having the sample tray formed into a quadrangle is placed on the top of the lamp chamber, it is possible to eliminate a protrusion from the front of the atomic absorption spectrophotometer. This prevents a person or something from colliding with the autosampler that requires the high accuracy, and also can reduces the mounted area of the atomic absorption spectrophotometer.

In addition, according to the first and second embodiments, because the autosampler is placed on the top of the lamp chamber, the autosampler conventionally placed in the front part of the graphite furnace analyzing section is excluded, which makes it possible to easily perform the maintenance of the graphite furnace analyzing section.

Moreover, in the first and second embodiments, the driving mechanism for driving the arm of the autosampler includes the driving mechanism for driving the arm in left and right directions, and the driving mechanism for driving the arm in up and down directions. In addition to it, both of the mechanisms are configured independently to each other, eliminating the need for driving in the depth direction. Accordingly, it is possible to perform adjustment, and control, of the sampler easier than the autosampler that drives its arm in X, Y, Z directions, and than the autosampler of the rotary method that controls its arm by a length, and an angle, of the arm.

Furthermore, in the autosampler used in the first and second embodiments, because samples are arranged into an array lengthwise and crosswise on the sample tray so as to form a quadrangle, a microplate which is used for general purpose applications in the genetic research field, and the like, can be used as a reagent tray.

As described above, according to the present invention, the following effects are produced: the mounted area of the atomic absorption spectrophotometer can be reduced; the autosampler can be easily adjusted with a high degree of accuracy; and its maintenance can be easily performed.

What is claimed is:

1. An atomic absorption spectrophotometer comprising:
   a lamp chamber for housing plural hollow cathode lamps;
   a flame gas controller;
   an analyzing chamber placed between the lamp chamber and the flame gas controller, and
   an optical path through which a luminous flux travels in a straight line from the lamp chamber up to the analyzing chamber;
   wherein an autosampler having a sample tray is placed on the top of the lamp chamber or on the top of the frame flame gas controller.

2. An atomic absorption spectrophotometer according to claim 1, wherein:
   said sample tray includes a large number of sample bottles which are arranged into an array lengthwise and crosswise on a quadrangular tray, and plural reagent bottles which are aligned in the lateral direction behind the sample bottles;
   said autosampler comprising:
   an X-axis driving mechanics which is placed behind the sample tray, and makes an arm for holding an aspiration needle drive in the lateral direction;
   a Y-axis driving mechanics which holds the sample tray at the position under the sample tray, and makes the sample tray move in the depth direction;
   the X-axis driving mechanics and the Y-axis driving mechanics being used to select a sample.

3. An atomic absorption spectrophotometer according to claim 2, comprising:
   a housing section for units provided behind the lamp chamber, the analyzing chamber, and the flame gas controller, which are arranged along the optical path,
   wherein in the housing section, a power unit is placed at the lower position, an optical unit having a photomultiplier is placed at the middle position, and the X-axis driving mechanics of the autosampler is placed at the upper position.

4. An atomic absorption spectrophotometer according to claim 3, wherein:
   a control circuit board for controlling the whole atomic absorption spectrophotometer is placed in the upper position of said housing section.

5. An atomic absorption spectrophotometer according to claim 1, wherein:
   said analyzing chamber constitutes a graphite furnace analyzing section, and which is equipped with a door on the front surface, the maintenance inside the graphite furnace analyzing section can be performed through the door from the front side of the atomic absorption spectrophotometer.

6. An atomic absorption spectrophotometer according to claim 2, comprising:
   a microplate can be held on the sample tray instead of the sample bottles.

7. An atomic absorption spectrophotometer, wherein:
   a lamp chamber for hollow cathode lamps, a flame gas controller, and an analyzing chamber are arranged at the front part of the upper surface of a bottom panel used as the base; the analyzing chamber is placed between the lamp chamber and the flame gas controller; a housing section for units is placed at the rear part of the bottom panel;
   the height of said housing section is set higher than those of the analyzing chamber, the lamp chamber, and the flame gas controller, which are placed in front of said housing section;
   an optical path through which a luminous flux emitted by the hollow cathode travels, is provided from the lamp chamber up to the flame gas controller;
   an autosampler having a sample tray is placed on the top of the lamp chamber or on the top of the flame gas controller; and
   said autosampler comprising:
   an X-axis driving mechanics which is provided in the housing section, and makes an arm for holding an aspiration needle drive in the lateral direction;
   a Y-axis driving mechanics which holds the sample tray at the position under the sample tray, and makes the sample tray move in the depth direction;
   the X-axis driving mechanics and the Y-axis driving mechanics being used to select a sample.

8. An atomic absorption spectrophotometer according to claim 7, wherein:
   said sample tray includes a large number of sample bottles which are arranged into an array lengthwise and crosswise on a quadrangular tray, and reagent bottles which are aligned in the lateral direction behind the large number of sample bottles.

9. An atomic absorption spectrophotometer according to claim 7, wherein:
   said housing section for units is formed into a box-shape, and placed behind the lamp chamber, the flame gas controller, and the analyzing chamber;
   wherein in the housing section, a power unit is placed at the lower position, an optical unit having a photomultiplier is placed at the middle position, and a control circuit board for controlling the whole atomic absorption spectrophotometer as well as the X-axis driving mechanics of the autosampler is placed at the upper position.

* * * * *